(12) United States Patent
Watson et al.

(10) Patent No.: US 7,113,625 B2
(45) Date of Patent: Sep. 26, 2006

(54) SYSTEM AND METHOD FOR IMAGE ANALYSIS OF SLIDES

(75) Inventors: Matthew C. Watson, Mission Viejo, CA (US); Suresh Venkatraman, Ladera Ranch, CA (US); Matt Tate, Saint Charles, IL (US)

(73) Assignee: U.S. Pathology Labs, Inc., Irvine, CA (US)

( * ) Notice: Subject to any disclaimer, the term of this patent is extended or adjusted under 35 U.S.C. 154(b) by 0 days.

(21) Appl. No.: 11/035,182

(22) Filed: Jan. 13, 2005

(65) Prior Publication Data

US 2006/0072804 A1     Apr. 6, 2006

Related U.S. Application Data

(60) Provisional application No. 60/615,215, filed on Oct. 1, 2004.

(51) Int. Cl.
*G06K 9/00* (2006.01)
(52) U.S. Cl. .......................... 382/133; 382/128; 436/63
(58) Field of Classification Search ................ 382/128, 382/129, 130, 131, 132, 133, 134, 255, 286, 382/289, 291, 312; 435/4, 6, 63, 64, 325, 435/23; 396/56; 436/46, 63, 64, 74, 519; 427/2.11
See application file for complete search history.

(56) References Cited

U.S. PATENT DOCUMENTS

| | | | | |
|---|---|---|---|---|
| 5,352,613 A | * | 10/1994 | Tafas et al. .................... 436/63 |
| 5,647,025 A | | 7/1997 | Frost et al. |
| 5,671,288 A | * | 9/1997 | Wilhelm et al. ............ 382/128 |
| 5,790,710 A | | 8/1998 | Price et al. |
| 5,891,619 A | * | 4/1999 | Zakim et al. .................. 435/4 |
| 6,007,996 A | * | 12/1999 | McNamara et al. ........... 435/6 |
| 6,101,265 A | | 8/2000 | Bacus et al. |
| 6,151,405 A | | 11/2000 | Douglass et al. |
| 6,195,474 B1 | * | 2/2001 | Snyder et al. ............... 382/312 |
| 6,215,892 B1 | | 4/2001 | Douglass et al. |
| 6,330,349 B1 | | 12/2001 | Hays et al. |
| 6,396,941 B1 | * | 5/2002 | Bacus et al. ................ 382/128 |

(Continued)

FOREIGN PATENT DOCUMENTS

WO          WO/9609598           3/1996

OTHER PUBLICATIONS

ScanScope User Guide Revision 2, Mar. 11, 2004.

(Continued)

*Primary Examiner*—Jingge Wu
*Assistant Examiner*—Abolfazl Tabatabai
(74) *Attorney, Agent, or Firm*—Vista IP Law Group LLP (57) ABSTRACT

A method of analyzing images of stained slides on a remote client computer connected to a wide area network such as the Internet includes the steps of scanning a stained slide to produce a digital image file of the stained slide and storing the digital image at a first location. An image viewer and analysis program is executed on a client computer in a location remote from the first location. A stored digital image from the first location is transferred to the client computer. A user selects a field from the stored digital image using the image and analysis viewer program. The field is then scored either manually or automatically. A user may also score a section of a field. Multiple fields and/or sections may be scored to achieve an overall score for the slide. A hardcopy report may be generated based on the scoring.

19 Claims, 10 Drawing Sheets

U.S. PATENT DOCUMENTS

| | | |
|---|---|---|
| 6,404,916 B1 | 6/2002 | De La Torre-Bueno |
| 6,418,236 B1 | 7/2002 | Ellis et al. |
| 6,445,817 B1 | 9/2002 | de la Torre-Bueno |
| 6,518,554 B1 | 2/2003 | Zhang |
| 6,546,123 B1 | 4/2003 | McLaren et al. |
| 6,553,135 B1 | 4/2003 | Douglass et al. |
| 6,631,203 B1 | 10/2003 | Ellis et al. |
| 6,656,683 B1 * | 12/2003 | Reuben et al. ................ 435/6 |
| 6,671,393 B1 | 12/2003 | Hays et al. |
| 6,674,896 B1 | 1/2004 | Torre-Bueno |
| 6,697,509 B1 | 2/2004 | De La Torre-Bueno |
| 6,711,283 B1 | 3/2004 | Soenksen |
| 6,718,053 B1 | 4/2004 | Ellis et al. |
| 6,800,249 B1 | 10/2004 | De La Torre-Bueno |
| 2003/0168577 A1 | 9/2003 | Zhang |
| 2004/0066960 A1 | 4/2004 | McLaren et al. |
| 2004/0071327 A1 | 4/2004 | Ellis et al. |

OTHER PUBLICATIONS

Bernard Wolfson, Virtual Pathology Labs Speeds Results, Orange County Register, Sep. 21, 2004.

* cited by examiner

Fig. 1

Cases reported for the last 14 days
New Results to Print

| | Date Posted | Patient Name | Test Name | Accession Number | Medical Record# | Treating Physician | Specimen Status | Last Reviewed | Notes |
|---|---|---|---|---|---|---|---|---|---|
| 32a | 10/26/2004 12:00:00 AM | Unknown UNKNOWN | Prognostic Virtual Image Technical | APC04-006172 | NOT GIVEN | | Complete | 10/29/2004 10:04:39 AM | Notes |
| 32b | 10/26/2004 12:00:00 AM | Unknown UNKNOWN | Prognostic Virtual Image Technical | APC04-006512 | | | Complete | 10/29/2004 10:05:10 AM | Notes |
| 32c | 10/26/2004 12:00:00 AM | Unknown UNKNOWN | Prognostic Virtual Image Technical | APC04-006515 | | | Complete | 10/29/2004 10:25:19 AM | Notes |
| 32d | 10/26/2004 12:00:00 AM | Unknown UNKNOWN | Prognostic Virtual Image Technical | APC04-006513 | | | Complete | 10/29/2004 8:46:49 AM | Notes |
| 32e | 10/26/2004 12:00:00 AM | Unknown UNKNOWN | Prognostic Virtual Image Technical | APC04-006516 | | | Complete | 10/29/2004 10:24:46 AM | Notes |
| 32f | 10/26/2004 12:00:00 AM | Unknown UNKNOWN | Prognostic Virtual Image Technical | APC04-006514 | | | Complete | 10/29/2004 6:33:16 AM | Notes |

SYSTEM AND METHOD FOR IMAGE ANALYSIS OF SLIDES

RELATED APPLICATION

This application claims priority to U.S. provisional patent application Ser. No. 60/615,215 filed on Oct. 1, 2004. The above-identified U.S. provisional patent application is incorporated by reference as if set forth fully herein.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The field of the invention generally relates to systems and methods used to image and analyze slides containing stained biological material. More specifically, the field of the invention relates to systems and methods used to image and analyze slides containing stained biological material over a wide area network (WAN) such as the Internet.

BACKGROUND OF THE INVENTION

Immunohistochemistry (IHC) is often used to diagnose suspect biological material. In addition, IHC techniques can be used prognostically to assist clinical decision makers. Typically, a source of biological material such as tissue is sent to a dedicated laboratory which then undergoes histological processing. Histology processing includes, for example, processing of tissue samples to fix and preserve the tissue samples. Fixing the tissue samples prevents degradation and stops the cells from changing characteristics. After fixation, tissue samples are then stained with one or more stains. The stained samples are contained on slides which can then be imaged for subsequent viewing.

Certain stains enable the pathologist to see the cellular structure and morphology under a microscope more easily. Still other stains or markers are antigen-specific and preferentially bind or otherwise associate with diseased tissue (e.g., cancerous tissue). These antigen-specific stains or markers can be used by a pathologist (or other trained professional) to score a particular slide.

For example, under prior testing processes, a client would send a tissue specimen and test request to a dedicated laboratory. The laboratory would then stain the slides with the appropriate IHC markers and, when ordered, provide a quantitative analysis of the sample using a computer that was directly associated with or otherwise locally connected to an imaging device such as a scanner. The images and any analysis are generated on a report using the computer associated with or locally connected to the imaging device. The images are then burned to a portable storage medium such as, for example, a DVD and sent back to the client with the original slides. The client can view the images and is given the option to supplement or alter the report using their professional interpretation.

There are several disadvantages, however, with a system and method like the one described above. First, because the images are stored on a DVD (or the like) and sent back to the client, there is a significant delay in the amount of time it takes for a pathologist or other trained health professional to review the slide. This delay can amount to several days. This delay can be troubling from a psychological perspective of the patient (e.g., waiting for the results of a breast biopsy for possible cancer). In addition, if diagnosis can be made soon after a sample is prepared and imaged, the patient can be treated that much sooner. In the case of cancer diagnosis, the patient can immediately start undergoing chemotherapy—a potentially life saving advantage over current methods. In addition to the delay, there is an increased cost of delivering the image-files via the mail or by way of courier.

The current method of delivering digital images to pathologists on DVDs (or other portable media) also restricts the ability to get multiple opinions from professionals located in different geographic locations. For example, using current practices, the same DVD would have to be forwarded to different pathologists in order to obtain multiple opinions (or multiple DVDs sent out simultaneously). This cumbersome and time-consuming procedure prevents patient's from obtaining multiple opinions on a timely basis.

Another disadvantage of the current system and method is that additional stains are often employed on a sample based on the initial results or scoring of a slide. For example, a physician may order a screening test for cancer which employs a broad-based or general stain. If this test is positive for cancer, the physician may follow-up with one or more additional tests using other stains which are more specific (e.g., stains which may identify whether a particular cancer is highly metastatic). Using the current system, several days (or more) are lost in sending the initial slide images to the pathologist. It would be preferable if the slide images were available almost immediately after imaging. In this manner, subsequent staining and imaging of the sample may be accomplished without delay.

There thus is a need for system and method in which pathologists or other trained health care professionals have virtually immediate access to imaged slides. Such a system and method would decrease the amount of time necessary to diagnose a particular condition or diseased state. In addition, multiple opinions could be obtained without the need to deliver images stored on a portable storage medium. The system and method would preferably permit a physician or other health care professional to order additional staining tests on a timely basis. Finally, the system and method would permit pathologists or other trained health care professionals to view and score slides from virtually any geographic location.

SUMMARY OF THE INVENTION

In one aspect of the invention, a method is described for providing images of stained slides to a remote client computer connected to a wide area network for analysis. A scanner is provided for imaging stained slides and producing a digital image file of the stained slides. A storage device is provided for storing digital image files for the stained slides. A client viewer program is provided on the remote client computer, the client viewer program capable of accessing one or more digital image files located on the storage device and displaying the one or more digital image files on the remote client computer. A slide analysis program is also provided on the remote client computer for analyzing the one or more digital image files.

In another aspect of the invention, a system is described for providing images of stained slides to a remote client computer connected to a wide area network. The system includes a scanner for imaging stained slides and producing a digital image file of the stained slides. The system also includes a storage device for storing digital image files for the stained slides, the storage device being connected to the wide area network. A remote client computer is also included in the system, the client computer having an image viewer and analysis program stored thereon, the image viewer and analysis program capable of accessing one or more digital image files located on the storage device via the wide area network and providing a score of a stained slide or a portion of a stained slide.

In another aspect of the invention, a method of analyzing images of stained slides on a remote client computer connected to a wide area network is described. A stained slide is scanned to produce a digital image file of the stained slide. This digital image is then stored at a first location. An image viewer and analysis program is executed on a client computer in a location remote from the first location. The stored digital image is then transferred from the first location to the client computer. A field from the stored digital image is then selected using the image viewer and analysis program. Finally, the selected field is scored. The above-described method may also be implemented using a portion or section of a selected field. Individual fields and/or sections may be scored. In addition, an overall score for a slide based on individual scores of several fields and/or sections is also possible.

It is an object of the invention to provide a system and method which permits remote viewing and analysis of a stained slide immediately after scanning. It is yet another object of the invention to provide a system and method which allows a user to select multiple fields and/or sections of a stained slide for subsequent imaging and analysis. It is still another object of the invention to provide a system and method which allows a user to manually or automatically score selected field(s) or section(s) of a stained slide using a client computer which is remotely located away from scanning site. It is yet another object of the invention to provide a system and method which permits the dissemination of stained slide images to physicians without the need for portable storage media. These and other objects are described in more detail below.

BRIEF DESCRIPTION OF THE DRAWINGS

FIG. 5 illustrates a score (3+) for a stain for HER.

FIG. 6 illustrates an image analysis screen which is used to score a slide or a particular field or section of a slide. FIG. 6 illustrates a percent positivity score for a section of slide which was manually selected using a free-hand drawings tool.

DETAILED DESCRIPTION OF THE INVENTION

Figure 1:
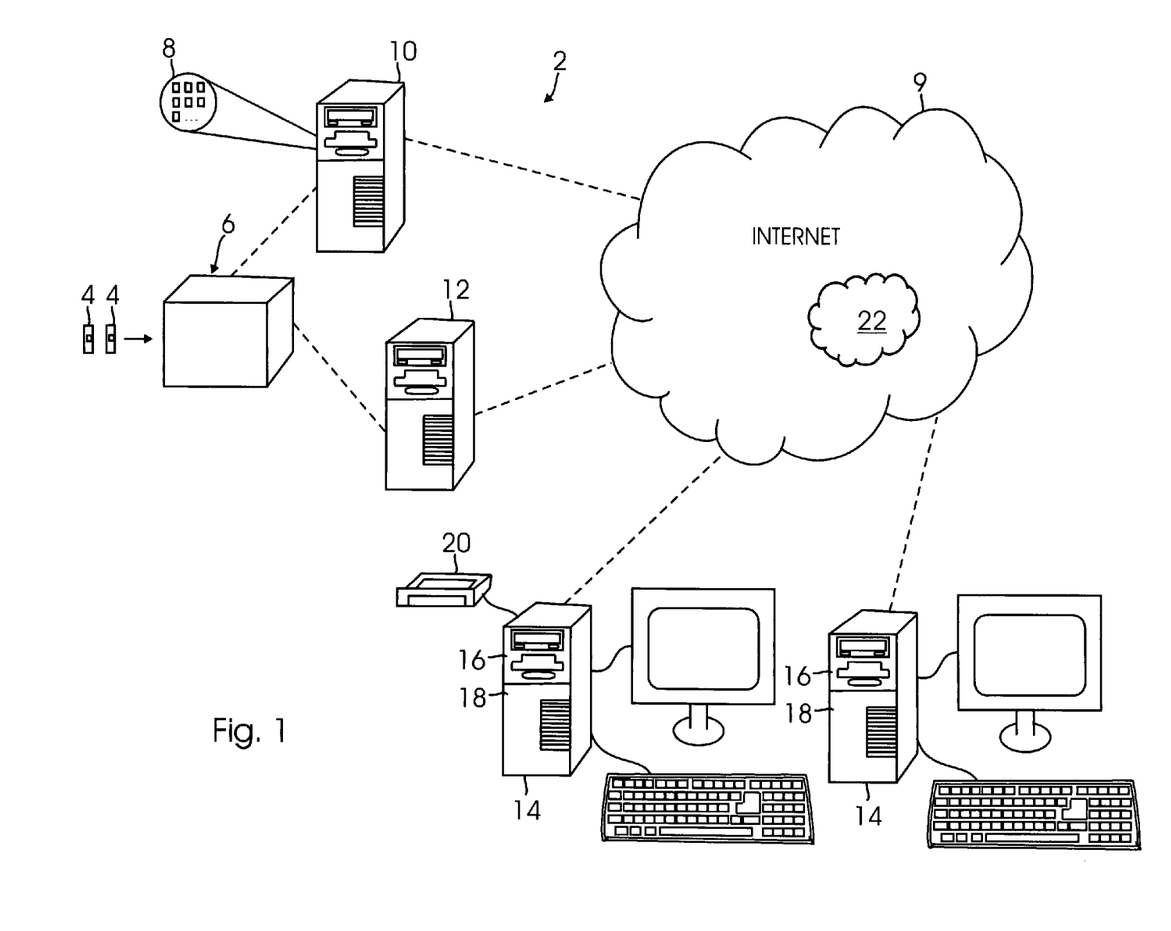
FIG. 1 illustrates a system used to image and remotely view and score images of stained slides.

FIG. 1 illustrates a system 2 used to image and remotely view and score images of stained slides 4. The system 2 includes a scanner 6 capable of scanning the stained slides 4 and producing digital image files 8 of the scanned slides 4. One possible scanner 6 which can be used in accordance with the present invention is the SCANSCOPE T2 scanner available from Aperio Technologies, Inc., 1430 Vantage Court, Suite 106 Vista, Calif. 92083. The digital image files 8 are stored on a network-accessible storage device 10 such as a computer. Preferably, the digital image files 8 are stored in TIFF or JPEG format. In a preferred aspect of the invention, the network-accessible storage device 10 comprises an image server which contains one or more storage devices such as hard drives for storing the digital image files 8. The image server is connected to a WAN 9 such as, for example, the Internet to allow access by remote users as described in more detail below.

The system 2 further includes a database server 12 for storing information pertaining to the scanned slide 4. This information includes such things as patient name, test name, accession number, ordering physician, specimen ID, collection date, received date, medical record number, treating physician name, case name, case number, file path of image on image server, stains used, user ID, user password, and the like. The database server 12 is also connected or otherwise linked to the WAN 9 such that this information may be accessible as described below.

The system 2 further includes at least one client computer 14 which is connected or otherwise linked to the WAN 9, such as the Internet. The client computer 14 is connected to the WAN 9 using, for example, a dedicated network connection, a DSL or cable modem, a wireless internet connection, a dial-up modem, or the like. The client computer 14 preferably includes a monitor or screen as well as an input device such as a keyboard and mouse. The client computer 14 includes a web or Internet browser stored thereon which is used (as described below) to access the individual digital image files 8 of the slides 4. The client computer 14 includes a client viewer program 16 stored thereon. The client viewer program 16 may be downloaded to the client computer 14 from a remotely located server. As described in more detail below, the client viewer program 16 permits a user to view and select different fields and/or sections of the digital image file 8 of the slide 4.

Still referring to FIG. 1, the system 2 also includes a slide analysis program 18 stored thereon. In one aspect, the slide analysis program 18 may be separate from the client viewer program 16. In another preferred aspect, however, the client viewer program 16 is integrated with the slide analysis program 18. In this latter aspect of the invention, the user would simply download a single program on the client computer 14 which has both viewing and analysis capabilities. Preferably the client viewer program 16 and slide analysis program 18 may be updated automatically or periodically by a remotely located server such that the user has the most recent tools and analysis algorithms for scoring a slide 4.

The client computer 14 is preferably connected to a printer 20 or other output device that is able to generate a written or hardcopy report of the analysis for a particular slide 4. The report may include scores which are generated automatically or input manually by a pathologist or other trained professional.

Figure 2:
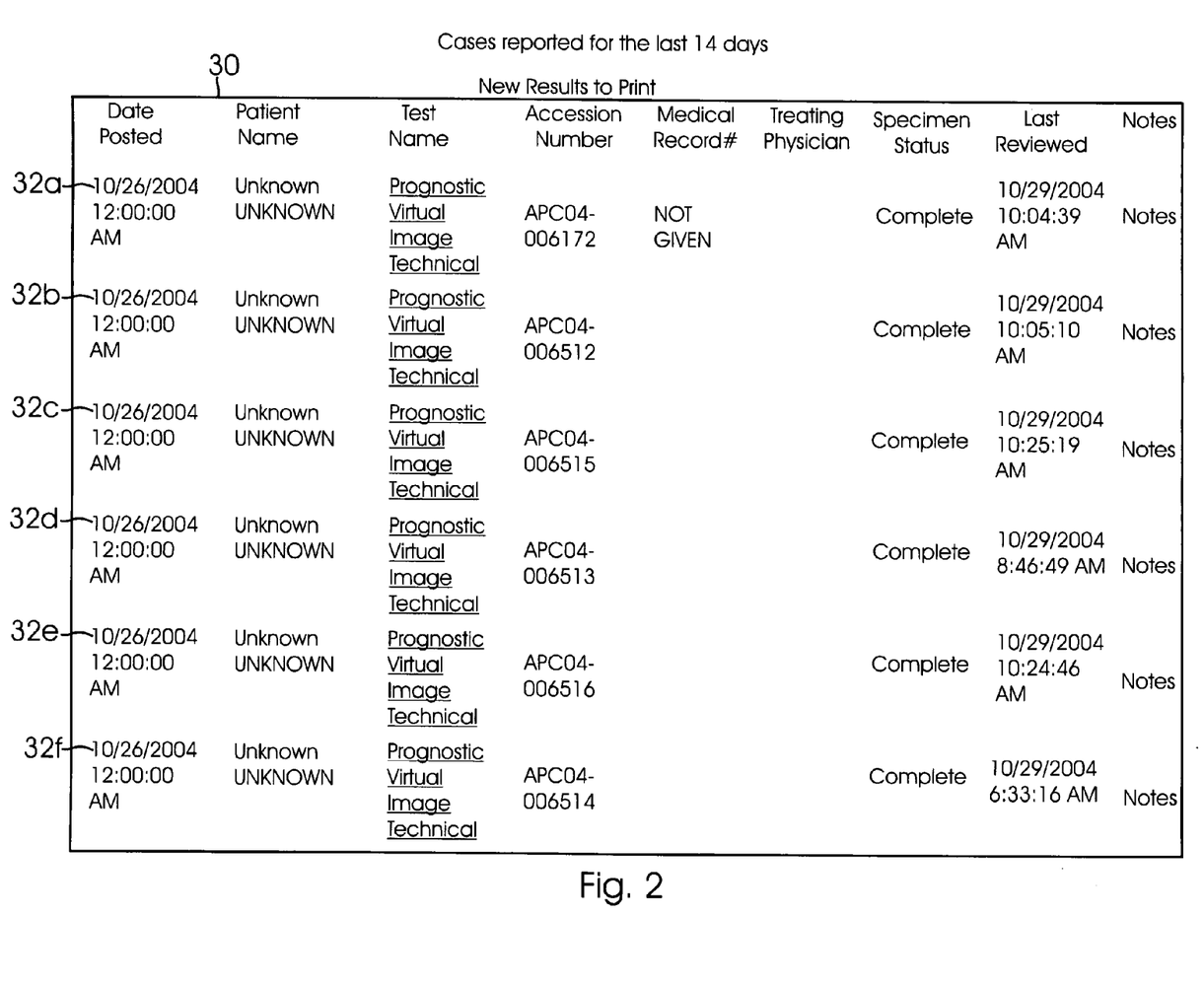
FIG. 2 illustrates a worklist page which is accessed by one or more client computers via a WAN such as the Internet.

FIG. 2 illustrates a worklist page 30 which accessed by directing the web or Internet browser on one of the client computers 14 to a portal 22 which is used to access the system 2. Access to the digital image files 8 as well as the other information stored in the database server 12 is preferably limited by use of a login ID and password. The worklist page 30 identifies particular cases 32(a)–32(f) in which tissue samples have been stained, fixed, imaged, and stored for subsequent viewing and analysis. FIG. 2 illustrates all cases have been reported, for example, in the last two weeks. The worklist page 30 displays (if present) the date posted, the patient name, the test name, the accession number, the medical record number, the treating physician, the specimen status, the last reviewed date and time, as well as any notes that may accompany the case. This information is preferably obtained from the database server 12. It is important to note that cases are posted and are accessible by any client computer 14 having Internet access.

Figure 3A:
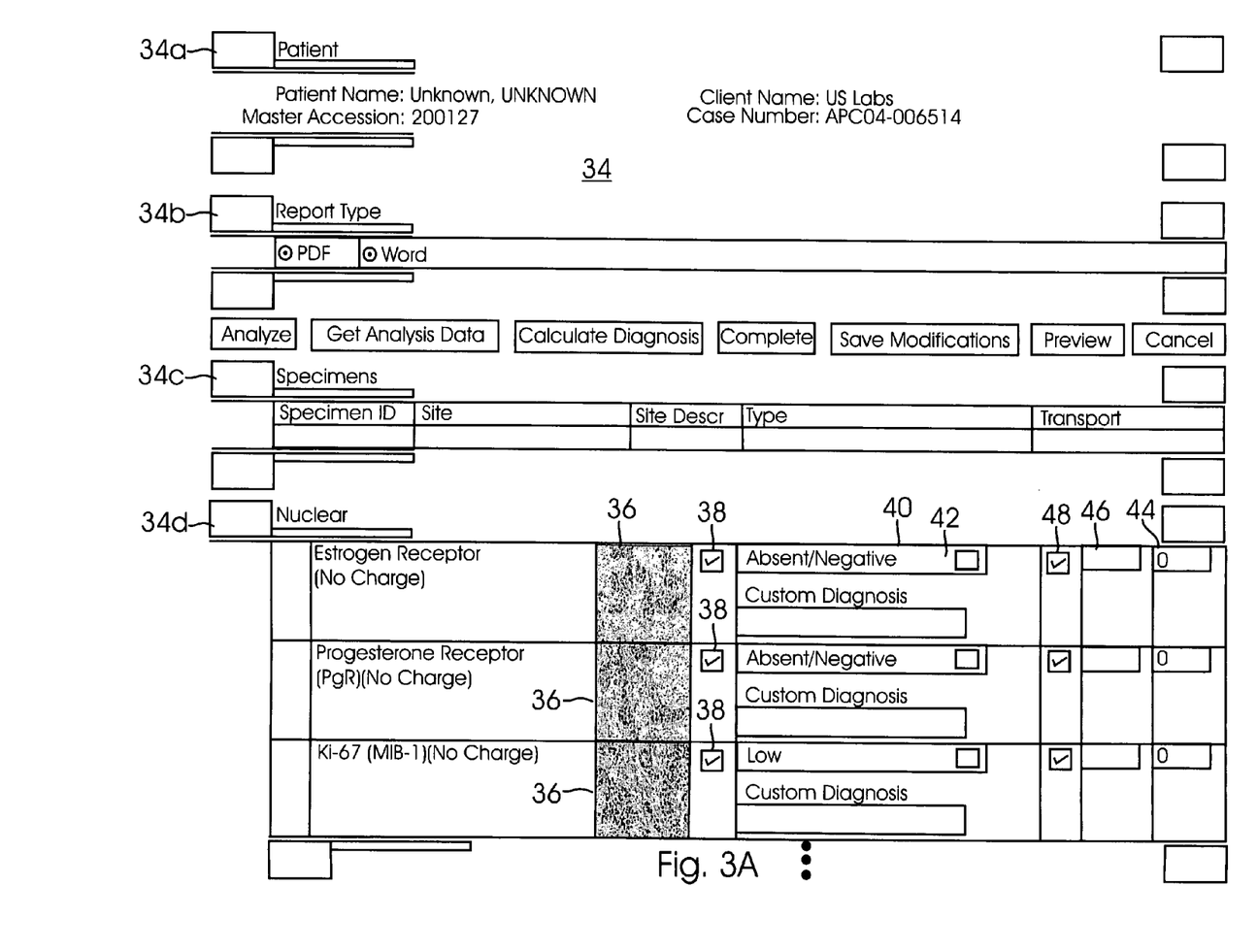
FIG. 3A illustrates a top portion of a profile page which is accessed through the worklist page of FIG. 2.
Figure 3B:
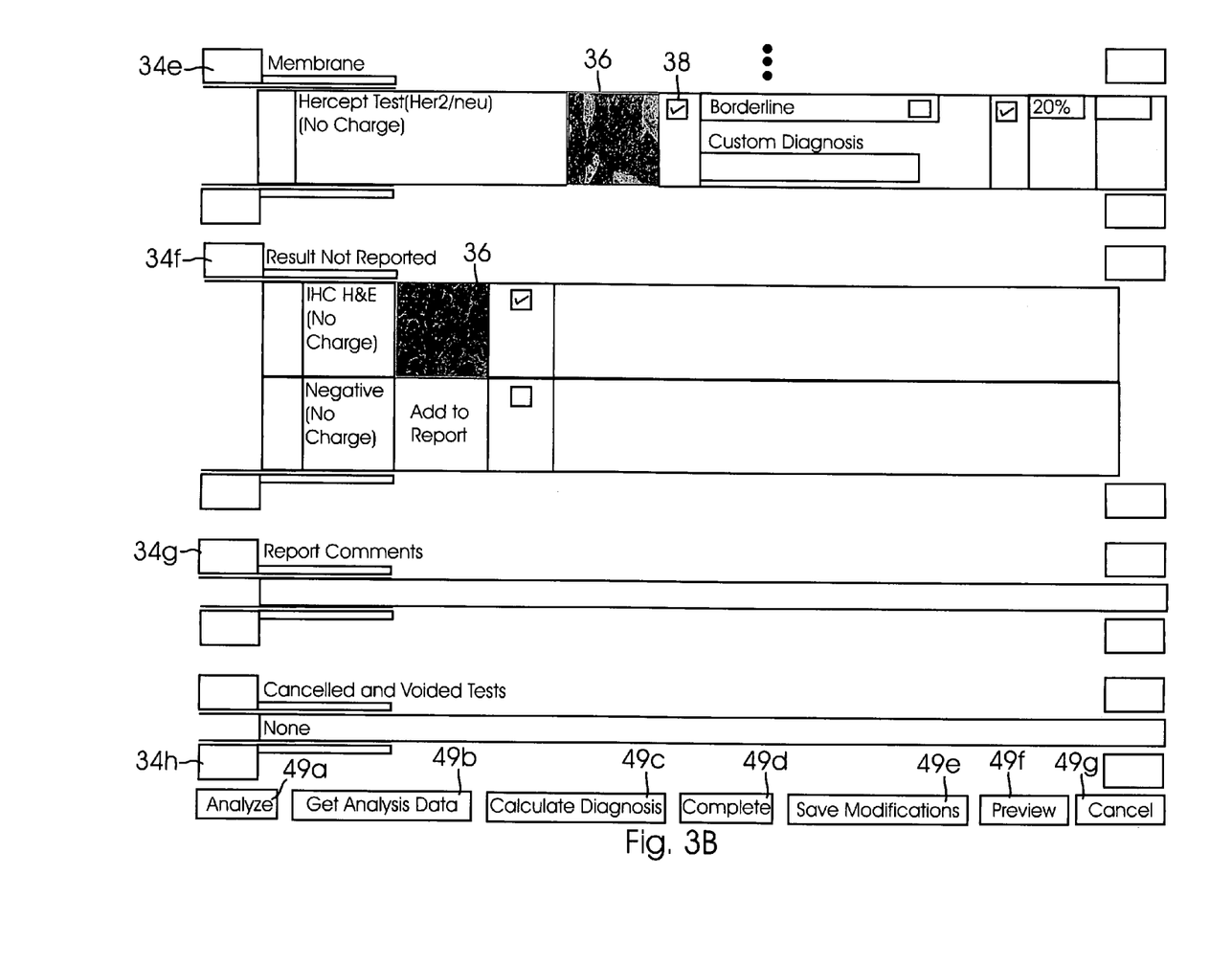
FIG. 3B illustrates a bottom portion of a profile page which is accessed through the worklist page of FIG. 2.

A user then clicks on an individual test name, which is hyperlinked, to access a profile page 34 as is shown in FIGS. 3A and 3B. The profile page 34 contains several subsections include a patient section 34(a), a report type section 34(b), a specimen section 34(c), a nuclear section 34(d) with respect to nuclear-based stains, and a membrane section 34(e) with respect to nuclear-based stains, an optional cytoplasmic section (not shown), a results not reported section 34(f), a report comments section 34(g), and cancelled or voided tests section 34(h). The patient section 34(a) includes the patient name, the master accession number, the client name, as well as the case number. The report type section 34(b) provides two radio buttons for two types of report formats: PDF and WORD. The specimen section 34(c) includes fields with respect to the specimen ID, site, site description, type (e.g., tissue type), and transport (e.g., paraffin embedded).

The profile page 34 also includes information pertaining to various stained images. Generally, stained images are broken down into a nuclear portion 34(d) (those stains which preferentially bind to features of the cell nucleus) and a membrane portion 34(e). For example, the nuclear portion 34(d) may include information obtained from a number of nuclear stains which bind or otherwise associate with, for example, estrogen receptor (ER), Ki-67, progesterone receptor (PR), and P53. The membrane portion 34(e) may include information obtained from a number of membrane stains which bind or otherwise associate with, for example, HER-2/Neu, and EGFR. Membrane testing is used, for example, to determine whether a breast carcinoma is positive for Her-2/Neu. Nuclear staining is used, for example, to determine the percentage of positive tumor cells stained for ER, PR, Ki-67 antigen (MIB-1), and p53 antigen. Cytoplasmic stain information (e.g., AE1, AE3, etc.) can also be included on the profile page 34. In addition, the profile page 34 may include a thumbnail image 36 and comment or diagnosis box for the stain combination of hematoxylin and eosin (IHC H&E). See FIG. 3B. In addition, the profile page 34 may include a negative control if desired.

Preferably, the profile page 34 includes a thumbnail image 36 or the like of a selected field or section of digital image file 8. The selected field or section is preferably selected by the user (as described in more detail below). The profile page also includes a check box 38 which, if checked, indicates that the digital image file 8 and other associated information will be included on the report that is generated. The profile page 34 also includes a diagnosis section 40 having a pull or drop down menu 42 which allows a user to give a pre-set diagnosis. The pre-set diagnosis options include: present/positive, absent/negative, borderline/low, and custom (which allows custom diagnosis).

The profile page 34 also includes, for each stain target, an intensity field 44 which contains a "score" of the intensity. Generally, in one aspect of the invention, the score in the intensity field ranges from 0 to 3. The score may be input manually by the user or, alternatively, the score may be automatically generated by the slide analysis program 18.

A percent positive field 46 is also included on the profile page 34 for each stain target. Generally, for a given digital image file 8, the image is scored by either the percent positive field 46 or intensity field 44. The percent positive field 46 contains a percentage figure corresponding to the percentage of stained target features in a selected field or section of a digital image file 8. This percentage may be input manually by the user or, alternatively, the score may be automatically generated by the slide analysis program 18. A check box 48 is also provided on the profile page 34 which, if checked, prints one or more reference ranges on the generated report. The reference range may include percentages which correspond to favorable or unfavorable results. The reference range may include, for example, scoring reference ranges (e.g., 0–1+ (not over-expressed), 2+ (borderline), 3+ (over-expressed).

Still referring to FIGS. 3A and 3B, the profile page 34 preferably includes a series of buttons 49 including an analyze button 49(a), a get analysis data button 49(b), a calculate diagnosis button 49(c), a complete button 49(d), a save modifications button 49(e), a preview button 49(f), and a cancel button 49(g).

The analyze button 49(a) is used to launch the client viewer program 16 described in more detail below. The get analysis button 49(b) is used to retrieve the analyzed data so that it can be reported. The calculate diagnosis button 49(c) is used to derive the diagnosis based on the values obtained from the image analysis algorithms. The diagnosis is calculated based on the reference ranges established for the particular test. Preferably, the user can change the reference range values on the profile page 34. The user then will click the diagnosis button 49(c) to get the appropriate diagnosis.

The complete button 49(d) is depressed when the user is ready to generate a report. The save modifications button 49(e) is used to save any modifications made on the profile page 34. Based on the security privileges that a particular user has, the user may not be able to preview or complete a case. The user will use the save modifications button 49(e) to save all the changes that have been made. The preview button 49(f) permits a user to preview the data and other information that will appear on the final report 82. The cancel button 49(g) is used to abort all the changes and transfer the user back to the worklist page 30.

Figure 4:
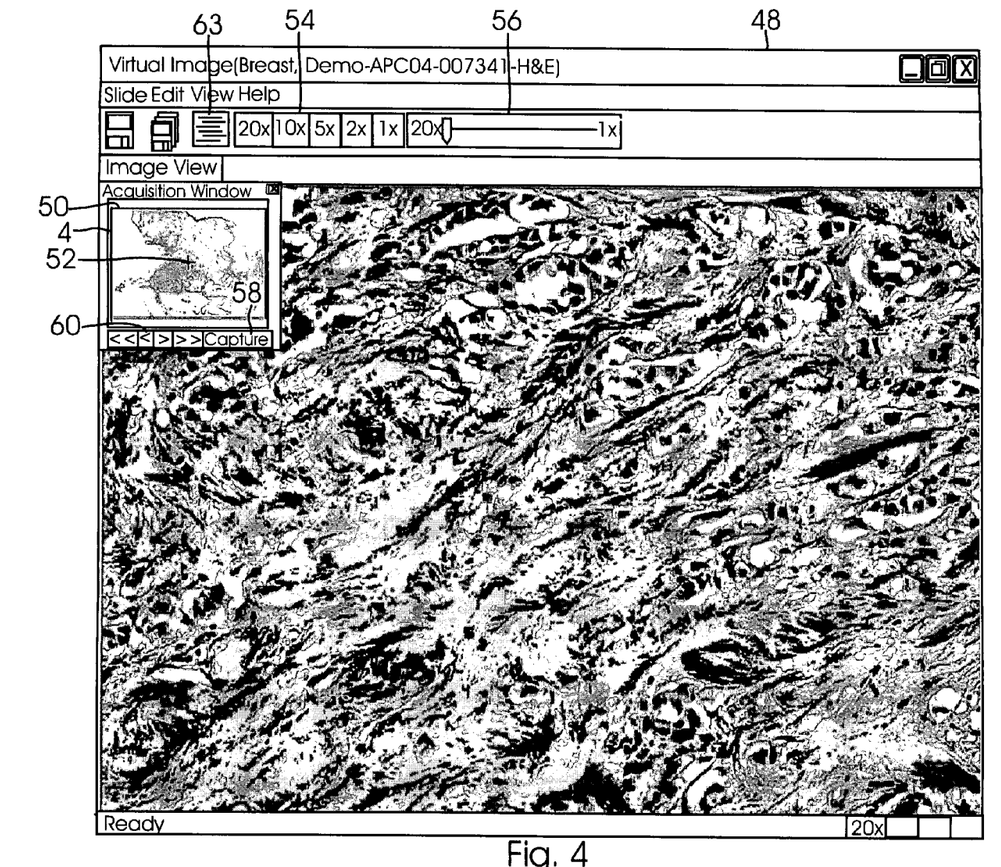
FIG. 4 illustrates an image viewing screen which is used to view a digital image file of a slide. The image viewing screen permits the user to alter the magnification level as well as move over different areas or regions of the digital image.

FIG. 4 illustrates an image viewing screen 48 which is launched or opened by the client viewer program 16. The image viewing screen 48 may be opened preferably by clicking on the analyze button 49(a) in the profile page 34. The image viewing screen 48 is preferably launched within a window such as those commonly used in WINDOWSbased software applications. The image viewing screen 48 preferably includes an acquisition window 50 which illustrates a view of all or substantially the entire imaged slide 4. The larger portion of the window shown in FIG. 4 contains a magnified view of a portion of the slide 4 shown in the acquisition window 50. Preferably, the acquisition window 50 includes a location identifier 52, for example, in the form of cross-hairs or the like which identifies which portion of the slide 4 is being displayed in the magnified view. This location identifier 52 can be moved, for example, using a mouse or the like to focus in on different regions of the slide 4. Preferably, the image of the slide in the image viewing screen 48 can be pulled in any direction to simulate movement as if on an actual microscope stage.

Still referring to FIG. 4, the viewer program 16 preferably permits the user to alter the degree of magnification of the magnified view. FIG. 4 illustrates a number of buttons 54 (e.g., 1×, 2×, 5×, 10×, and 20×) for different magnification levels. Alternatively, a sliding scale 56 may be used to alter the level of magnification. A user can capture a particular image of interest for subsequent viewing and/or analysis by pressing a capture button 58 on the image viewing screen 48. As seen in FIG. 4, the acquisition window 50 preferably includes navigation buttons 60 for moving between different digital image files 8 (e.g., slides 4).

Figure 5:
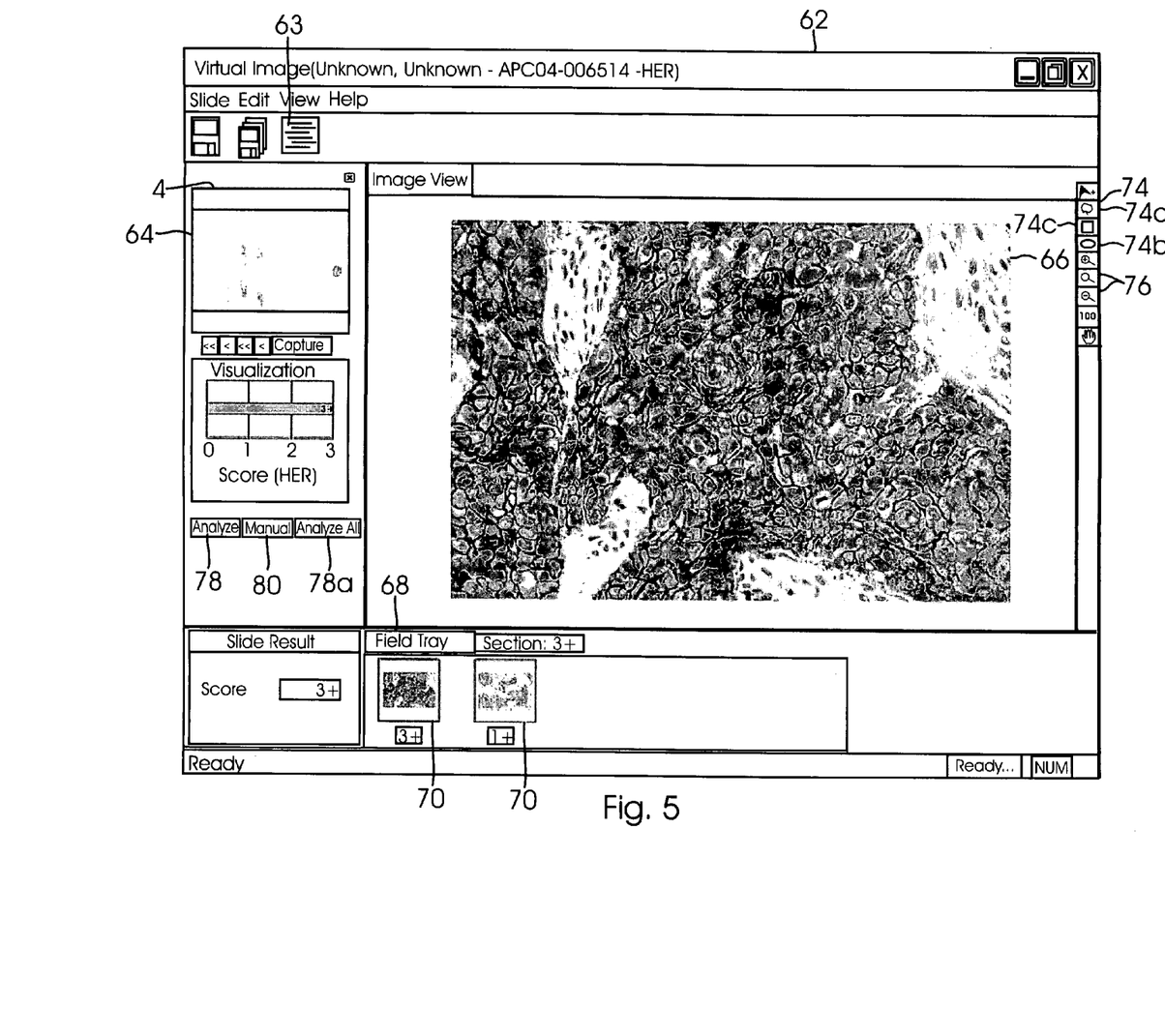
FIG. 5 illustrates an image analysis screen which is used to score a slide or a particular field or section of a slide.
Figure 6:
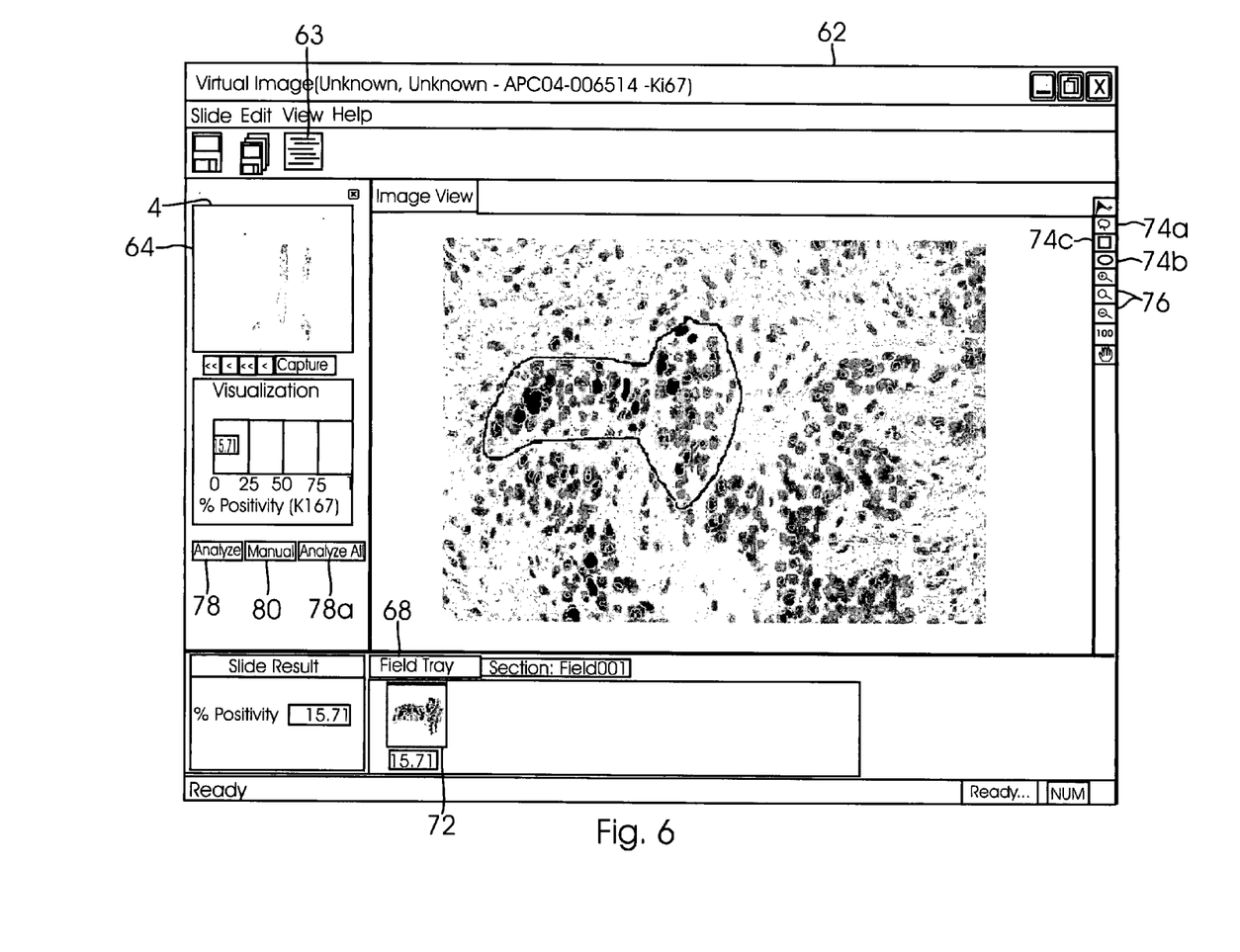

FIG. 5 illustrates an image analysis screen 62 which is launched by executing the slide analysis program 18. The image analysis screen 62 is preferably opened by clicking on a button 63 located on the image viewing screen 48 and image analysis screen. See FIGS. 4 and 5. The button 63 preferably is able to toggle between the imaging viewing screen 48 and the image analysis screen 62. As with the image viewing screen 48, the image analysis screen 62 is displayed in a window. The image analysis screen 62 includes a thumbnail picture 64 of the overall imaged slide 4. A larger magnified view of a captured field 66 is shown in FIG. 5. The image analysis screen 62 includes a field tray 68 in which a plurality of individual captured fields 70 are stored. The captured fields 70 may be captured by pressing on the capture button 58 as described above. In addition to fields 70, the field tray 68 can store individual sections 72. A section consists of a selected portion of a field 70. FIG. 6, for example, illustrates one such section 72 stored in the field tray 68.

Still referring to FIG. 5, the slide analysis program 18 includes a number of cutting tools 74. The cutting tools 74 permit a user to select a specific area of tissue within a captured field 70. The cutting tools 74 preferably include a free-hand draw tool 74(*a*), a drop circle or ellipse tool 74(*b*), and a drop box tool 74(*c*). The cutting tools 74 are used to select one or more sections 72. In addition, the slide analysis program 18 permits a user to magnify or reduce a captured field 70 by using a magnification tool 76.

The slide analysis program 18 also includes an analysis algorithm which automatically analyzes a selected field 70 or section 72 or even a portion of a selected field 70 or section 72. The slide analysis program 18 outputs a score and/or percent positivity of the selected field 70 or section 72 or sub-field or sub-section when the analyze button 78 is pressed. An analyze all button 78(*a*) is also provided which will then analyze all fields 70 or sections 72 present in the field tray 68. The slide analysis program 18 provides automatic scoring (i.e., score values or percent positivity values) of either or both the selected field 70/section 72 as well as the overall score value of the slide 4. With respect scoring the entire slide 4, this result is derived by averaging the total number of cells quantified from all selected fields 70 appearing in the field tray 68.

For nuclear stains, the algorithm in the slide analysis program 18 identifies cell nuclei (or cells) based on the shape, size, and color intensity. One exemplary algorithm identifies tumor cells based upon a set of parameters including cell size, cell shape, and nuclear chromatin staining pattern. Preferably, the algorithm includes pre-set threshold values for nucleus identification, epithelial area identification, staining classification, and staining. The pre-set threshold values may be modified to fine-tune the algorithm. For nucleus identification, threshold values or provided for nucleus size, nucleus brightness, size correction, nucleus separation, minimum nucleus size, and maximum nucleus size. For epithelial identification, epithelial intensity and circularity of nucleus are pre-set threshold values. For staining classification, the low, medium, and high intensity zones can be modified and set. Finally, with respect to staining, stain color control and staining percentage threshold levels can be established.

For membrane stains, the algorithm in the slide analysis program 18 identifies membranes (or cells) based on the membrane thickness, membrane completeness, and color intensity. Cytoplasmic staining is disregarded. In one exemplary algorithm, tumor cells are identified by a set of parameters including cell size, cell shape, and nuclear chromatin staining pattern. The algorithm determines the percentage of tumor cells showing complete circumferential membrane staining at weak, moderate, and strong levels of intensity (3+ or 2+); the percentage of cells showing incomplete membrane staining (1+); and the percentage of tumor cells with no membrane staining (0).

Figure 7:
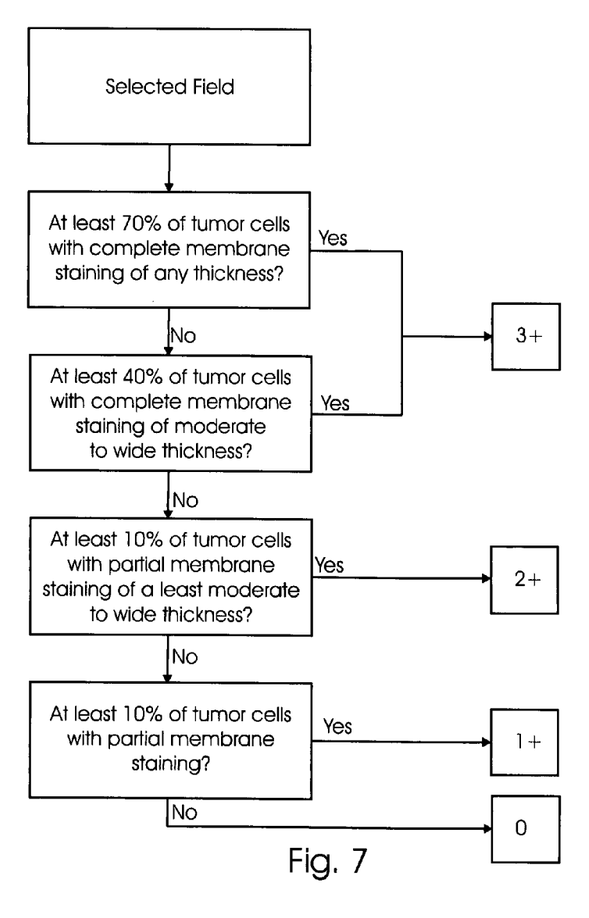
FIG. 7 illustrates one potential algorithm used to assign scores for a stained slide based on membrane staining.

FIG. 7 illustrates one potential algorithm used to assign scores for a stained slide 4 based on membrane staining. The stain scoring algorithm takes a tiered approach. Once the appropriate fields have been selected by the user, the image analysis program 18 first determines the percentage of cells staining at the 3+ level based upon an accounting of tumor cells that meet certain threshold levels for intensity and completeness of membrane staining. FIG. 7 illustrates a flow diagram for achieving scoring accuracy down to the 10% level. Membrane thickness is used by the image analysis software program 18 to account for membrane staining intensity. Cytoplasmic staining, if any, is ignored.

The pre-set threshold values may be modified to fine-tune the algorithm. Preferably, the algorithm includes pre-set threshold values for nucleus identification, epithelial area identification, membrane identification, membrane staining percentage, and membrane staining score clustering. For nucleus identification, nucleus size, nucleus radius, nucleus brightness, nucleus center identification mask, and nucleus identification by size (Sigma) are pre-set threshold values. For epithelial area identification, epithelial intensity is a pre-set threshold value. For membrane identification, membrane thickness and membrane staining are preset threshold values.

Preferably, the membrane staining percentage thresholds can be set for different scoring levels (i.e., 0+, 1+, 2+, and 3+). For membrane staining clustering, a combination of multiple membrane staining percentages can be set to assign an overall score. For example, a certain percentage of 3+ cells or a certain percentage of 2+ cells may produce an overall score of "3." The percentage ranges of the 3+ and 2+ cells which produce an overall score of "3" can preferably be pre-set and modified.

FIG. 5, for example, illustrates the score value for the selected field 70 (3+) as well as the score value for the overall slide 4 (3+). FIG. 6, for example, illustrates the percent positivity value of a single selected field 70 (15.71%) in addition to showing the percent positivity value of the slide 4 (15.71%). As seen in FIG. 6, section 72 was selected by using the free-hand draw tool 74(a). The outline of the selected section 72 is seen in the image analysis screen 62 in FIG. 6.

In a preferred aspect of the invention, the slide analysis program 18 provides a visual cue to the user of cellular features analyzed by the slide analysis program 18. The visual cue may include false coloring of cells or cellular features. The visual cue (initiated, for example, by hitting Ctrl-P key) is advantageous because the user is able to discern whether the algorithm in the slide analysis program 18 is properly identifying the correct features or cells used for scoring the field 70 or section 72. For example, false coloring may indicate that the slide analysis program 18 picked-up artifacts or the wrong cells or cellular features. The user can then select another field 70 or section 72 to score.

In one preferred aspect of the invention, for nuclear-based stains, a first color such as red is used to identify positive cell staining while a second color such as green is used to identify a negative cell. For membrane-based stains, a first color is used to identify a positive cell. In this case, the required thickness and completeness of membrane staining have been satisfied. A second color may be used to identify a positive cell which does not have complete membrane staining or required membrane thickness. A third color may be used to indicate membrane staining. A fourth color may be used to identify cytoplasmic staining. A fifth color may be used to identify a negative cell identified by the slide analysis program.

It is important to note that a user has the option to manually score a slide 4 or a field 70 or section of a slide 72. FIGS. 5 and 6 illustrate a manual button 80 which can be depressed to score the slide manually. Preferably, the manual button 80 permits a user to override the results that were automatically generated by the slide analysis program 18. In addition, the manual button 80 permits the user to input scoring data without having to push the analyze button 78. For example, certain slides 4 may be easily diagnosed just by visual inspection by the pathologist (or other trained professional). In this regard, the user does not incur the additional charge which would generally be incurred if the analyze button 78 were depressed.

The slide analysis program 18 permits the user to save the scoring data as well as the selected fields 70 or sections 72. Preferably, the profile page 34 is automatically populated with analysis data (e.g. selected imaged field 70 or imaged section 72 as well as scoring data). In one preferred aspect of the invention, the last field 70 or section 72 that is scored is posted to the profile page 34 as the thumbnail image 36. The profile page 34 shows a "snap-shot" of the entire case and allows a user to verify analysis information (such as the number of stains).

Once the profile page 34 is populated with the relevant information (either automatically or manually or a combination of both), a user is able to preview a report prior to creating a hardcopy version by using, for example, preview button 49(f). If any necessary edits are needed, the user is able to go back to the profile page 34 and alter or customize the appropriate fields.

Figure 8A:
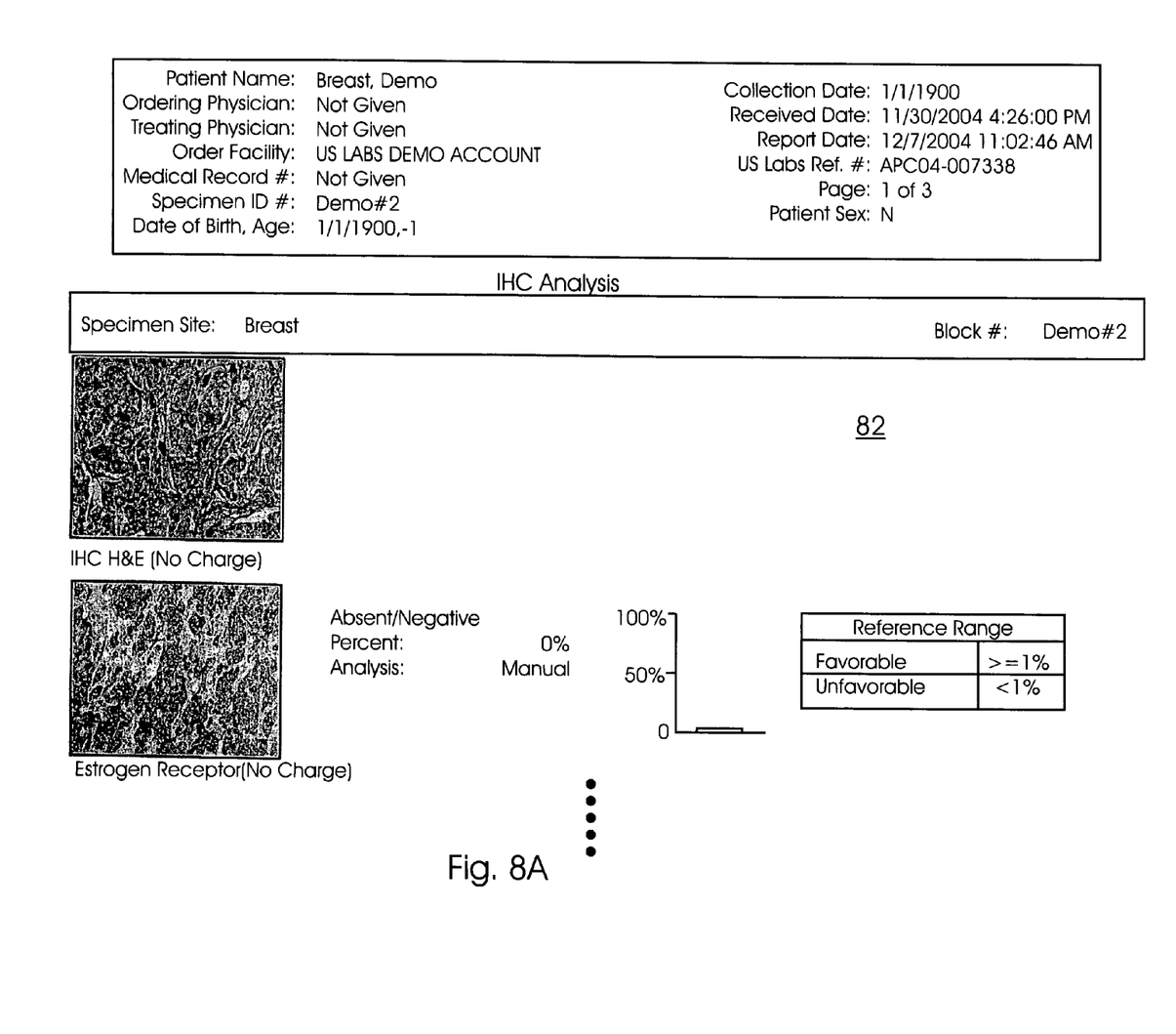
FIG. 8 illustrates a portion of a typical report generated on the client computer.
Figure 8B:
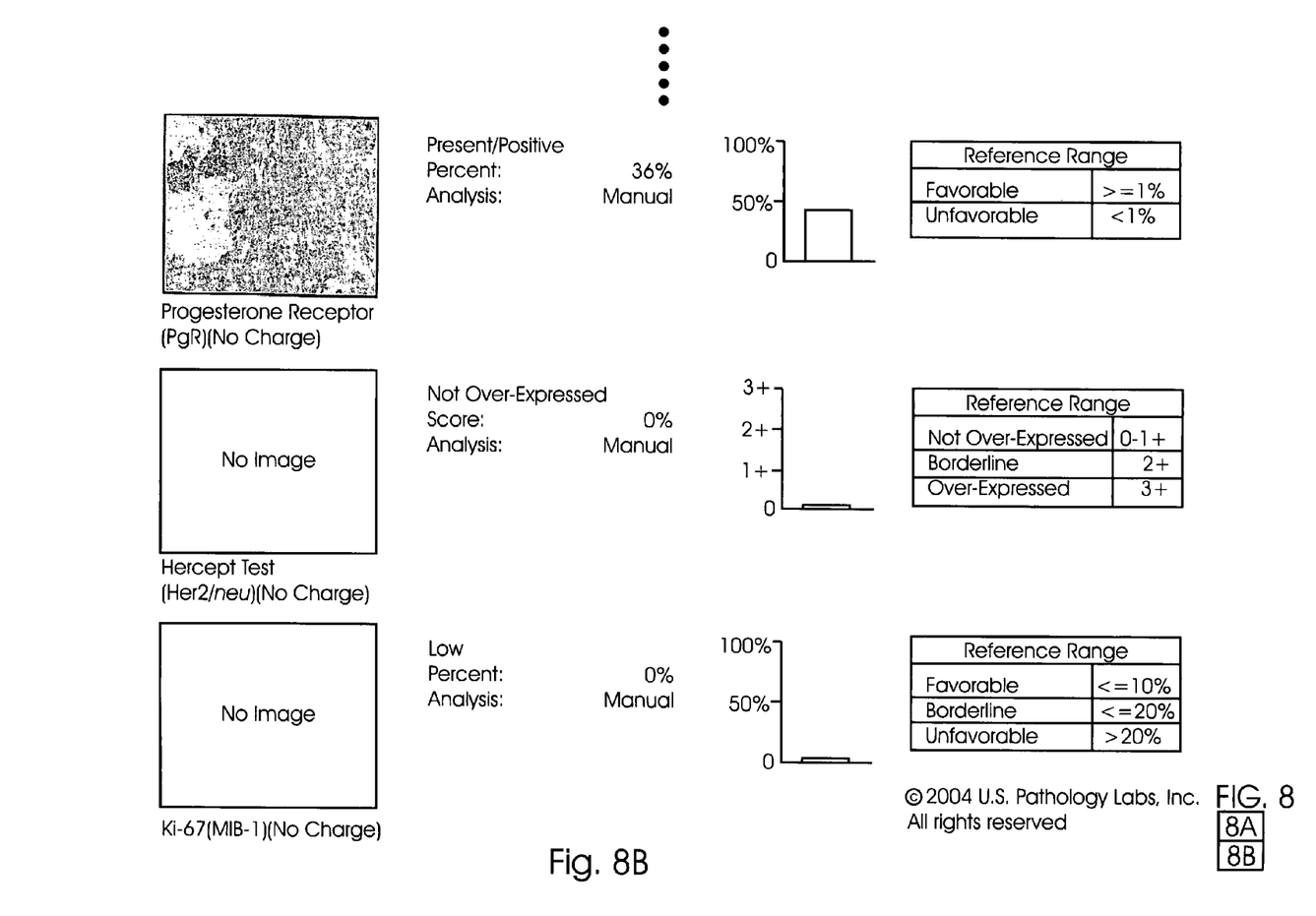

FIG. 8 illustrates a portion of a typical report 82 generated on the client computer 14. As stated above, the report 82 is preferably created in WORD or PDF format. Additional analysis such as DNA analysis data may be incorporated onto the report 82 (e.g., DNA ploidy/S-phase staining).

The above-described system 2 is able to provide rapid turn-around of stained slides 4 to a pathologist or physician. Preferably, digital image files 8 are posted to the web portal 22 within 48 hours of receipt of the sample. Even more preferable, the digital image files 8 are available for viewing and analysis within 24 hours of receipt of the sample.

While embodiments of the present invention have been shown and described, various modifications may be made without departing from the scope of the present invention. The invention, therefore, should not be limited, except to the following claims, and their equivalents.

We claim:

1. A method of providing images of stained slides to a remote client computer connected to a wide area network for analysis comprising the steps of:
   providing a scanner for imaging stained slides and producing a digital image file of the stained slides;
   providing a storage device for storing digital image files for the stained slides;
   providing a client viewer program on the remote client computer, the client viewer program capable of accessing one or more digital image files located on the storage device and displaying the one or more digital image files on the remote client computer; and
   providing a slide analysis program on the remote client computer for analyzing the one or more digital image files, wherein the slide analysis program provides a score of the slide or a portion of the slide.

2. The method of claim 1, wherein the client viewer program enables a user of the client computer to select and display one or more fields of the digital image files.

3. The method of claim 2, wherein the client viewer program enables a user of the client computer to manually select and display one or more sections from the one or more selected fields.

4. The method of claim 3, wherein the slide analysis program provides an average score based on a plurality of selected sections.

5. The method of claim 2, wherein the slide analysis program provides an average score based on a plurality of selected fields.

6. The method of claim 1, wherein the slide analysis program provides a visual cue to the user of cells or cellular features analyzed by the slide analysis program.

7. The method of claim 6, wherein the visual cue comprises false coloring of cells or cellular features, the false coloring being overlaid over at least a portion of the displayed digital image of the slide.

8. The method of claim 1, wherein the user has the option of automatically scoring an image or manually scoring an image.

9. The method of claim 1, further comprising the step of preparing a report based on the analysis.

10. A system for providing images of stained slides to a remote client computer connected to a wide area network comprising:
    a scanner for imaging stained slides and producing a digital image file of the stained slides;
    a storage device for storing digital image files for the stained slides, the storage device being connected to the wide area network; and
    a remote client computer, the client computer having an image viewer and analysis program stored thereon, the image viewer and analysis program capable of accessing one or more digital image files located on the storage device via the wide area network and providing a score of a stained slide or a portion of a stained slide.

11. The system of claim 10, wherein the image viewer and analysis program automatically scores the stained slide or a portion of the stained slide.

12. The system of claim 10, wherein the image viewer and analysis program provides an option for manual or automatic scoring.

13. The system of claim 10, wherein the image viewer and analysis program includes a report generation feature for generating a report containing scoring information for the stained slide or a portion of a stained slide.

14. A method of analyzing images of stained slides on a remote client computer connected to a wide area network comprising the steps of:

scanning a stained slide to produce a digital image file of the stained slide and storing the digital image at a first location;

executing an image viewer and analysis program on a client computer in a location remote from the first location;

transferring the stored digital image from the first location to the client computer;

selecting a field from the stored digital image using the image viewer and analysis program; and scoring the selected field using the image viewer and analysis program on the client computer.

15. The method of claim 14, wherein the step of scoring the selected field comprises manually scoring the field.

16. The method of claim 14, wherein the step of scoring the selected field comprises automatically scoring the field.

17. The method of claim 14, further comprising the step of selecting a section within the selected field.

18. The method of claim 17, further comprising the step of scoring the selected section.

19. The method of claim 17, wherein the step of selecting a section is performed using a tool selected from the group consisting of a free-hand draw tool, a drop circle, an ellipse tool, and a drop box tool.

* * * * *